(12) United States Patent
Grevious et al.

(10) Patent No.: US 8,644,948 B2
(45) Date of Patent: Feb. 4, 2014

(54) CONVERTER DEVICE FOR COMMUNICATING WITH MULTIPLE MEDICAL DEVICES

(75) Inventors: John J. Grevious, Minneapolis, MN (US); Yu Wang, Plymouth, MN (US); Michele A. Waldner, Hudson, WI (US)

(73) Assignee: Medtronic, Inc., Minneapolis, MN (US)

( * ) Notice: Subject to any disclaimer, the term of this patent is extended or adjusted under 35 U.S.C. 154(b) by 24 days.

(21) Appl. No.: 13/284,725

(22) Filed: Oct. 28, 2011

(65) Prior Publication Data

US 2013/0110202 A1    May 2, 2013

(51) Int. Cl.
*A61N 1/08*    (2006.01)

(52) U.S. Cl.
USPC .............................................. 607/60; 607/32

(58) Field of Classification Search
USPC ............. 128/903–904; 607/30–32, 59, 60, 65
See application file for complete search history.

(56) References Cited

U.S. PATENT DOCUMENTS

| | | | |
|---|---|---|---|
| 6,762,088 B2 | 7/2004 | Acosta et al. | |
| 6,804,558 B2 * | 10/2004 | Haller et al. ..................... | 607/30 |
| 7,203,549 B2 | 4/2007 | Schommer et al. | |
| 7,263,406 B2 | 8/2007 | Toy et al. | |
| 7,272,445 B2 | 9/2007 | Phillips et al. | |
| 7,356,369 B2 | 4/2008 | Phillips et al. | |
| 7,531,407 B2 | 5/2009 | Clevenger et al. | |
| 7,561,921 B2 | 7/2009 | Phillips et al. | |
| 7,631,415 B2 | 12/2009 | Phillips et al. | |
| 7,729,766 B2 | 6/2010 | Toy et al. | |
| 8,412,290 B2 * | 4/2013 | Shamim et al. ............ | 455/575.7 |
| 2009/0182388 A1 | 7/2009 | Von Arx et al. | |
| 2009/0248112 A1 | 10/2009 | Mumbru et al. | |
| 2009/0270948 A1 | 10/2009 | Nghiem et al. | |
| 2010/0168818 A1 | 7/2010 | Barror et al. | |
| 2010/0174348 A1 | 7/2010 | Bulkes et al. | |
| 2011/0087306 A1 | 4/2011 | Goossen et al. | |
| 2011/0134013 A1 | 6/2011 | Rawat et al. | |

FOREIGN PATENT DOCUMENTS

WO    2011070466 A1    6/2011

OTHER PUBLICATIONS

"RF Integrated Circuits for Medical Implants: Meeting the Challange of Ultra Low-Power Communication," Peter Bradley, Ph.D., Zarlink Semiconductor, 28 pgs., Aug. 2006.
"Medtronic N'Vision Clinician Programmer 8840 Technical Manual," 72 pgs., (2004).
International Search Report and Written Opinion from international application No. PCT/US2012/050691, dated Aug. 2, 2013, 12 pp.

* cited by examiner

*Primary Examiner* — Brian T Gedeon
(74) *Attorney, Agent, or Firm* — Shumaker & Sieffert, P.A.

(57) ABSTRACT

A device includes a housing, a radio-frequency (RF) antenna, a ground plane, an inductive telemetry antenna, and a processing module. The RF antenna is associated with the housing. The ground plane of the RF antenna is within the housing. The inductive telemetry antenna is within the housing and is disposed over a portion of the ground plane. The processing module is within the housing and is configured to communicate with a medical device using at least one of the RF antenna and the inductive telemetry antenna.

24 Claims, 9 Drawing Sheets

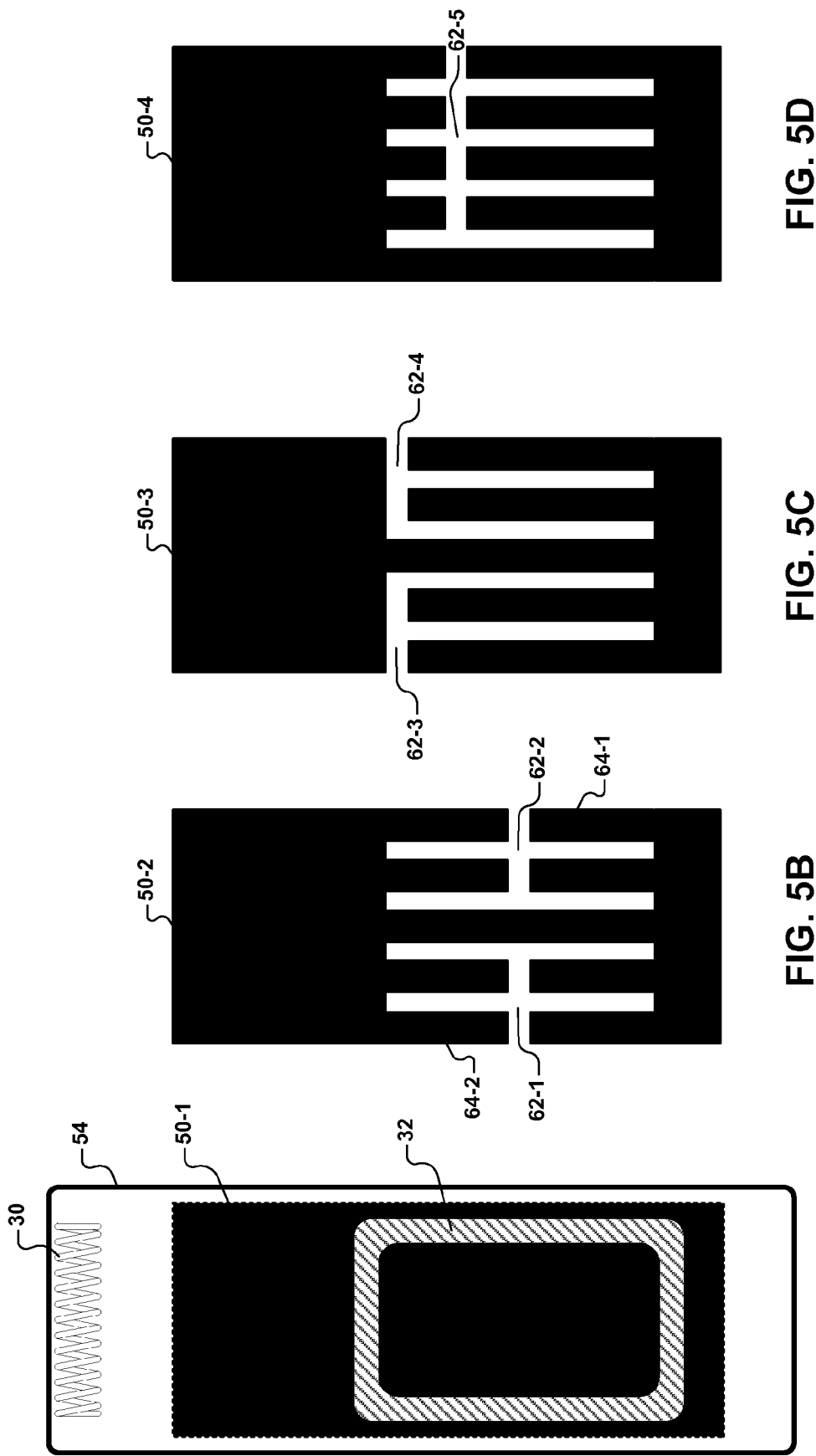

US 8,644,948 B2

CONVERTER DEVICE FOR COMMUNICATING WITH MULTIPLE MEDICAL DEVICES

TECHNICAL FIELD

The disclosure relates to a communication device, and more particularly, to a communication device for communicating with medical devices.

BACKGROUND

A variety of different types of medical devices may include wireless telemetry functionality. A clinician or a patient may use a programmer to wirelessly communicate with such medical devices. For example, a clinician or patient may use a programmer to wirelessly retrieve data from a medical device and to wirelessly program the medical device. Example medical devices including wireless telemetry functionality may include, but are not limited to, cardiac electrical therapy devices, neurostimulation devices, and drug pump devices.

Medical devices and programmers may communicate with one another using a variety of different wireless telemetry technologies. RF telemetry and inductive telemetry are two example wireless telemetry technologies that may be used by different medical devices and programmers. These different telemetry technologies may communicate in different frequency bands, include different antenna designs, communicate over a different range of distances, and transmit information at different data rates.

SUMMARY

A converter device of the present disclosure may serve as an intermediate communication device between a variety of different programmers and a variety of different medical devices that use different telemetry technologies. For example, the converter device may retrieve data from a medical device and then transmit the retrieved data to a programmer. Additionally, the converter device may retrieve data from the programmer and then transmit the retrieved data to the medical device. The converter device may include inductive telemetry and RF telemetry functionality for communication with different medical devices. The converter device may also include a more widely available communication technology for communicating with a programmer, e.g., Bluetooth, IEEE 802.11a/b/g/n, or a Universal Serial Bus (USB) standard (e.g., USB 1.0/2.0/3.0).

In some examples according to the present disclosure, a device comprises a housing, an RF antenna, a ground plane, an inductive telemetry antenna, and a processing module. The RF antenna is associated with the housing. The ground plane of the RF antenna is within the housing. The inductive telemetry antenna is within the housing and is disposed over a portion of the ground plane. The processing module is within the housing and is configured to communicate with a medical device using at least one of the RF antenna and the inductive telemetry antenna.

In some examples according to the present disclosure, a device comprises an RF antenna, a ground plane of the RF antenna, an inductive telemetry antenna, and a processing module. The inductive telemetry antenna is located over a portion of the ground plane. The ground plane defines one or more openings in the portion that is located under the inductive telemetry antenna. The processing module is configured to communicate with a medical device using at least one of the RF antenna and the inductive telemetry antenna.

In some examples according to the present disclosure, a device comprises an RF antenna, a ground plane of the RF antenna, a PCB, an inductive telemetry antenna, and a processing module. The PCB includes the ground plane of the RF antenna, and the RF antenna is mounted to the PCB. The inductive telemetry antenna is mounted on the PCB over a portion of the ground plane. The processing module is mounted on the PCB and is configured to communicate with a medical device using at least one of the RF antenna and the inductive telemetry antenna.

In some examples according to the present disclosure, a device comprises an RF antenna, a ground plane of the RF antenna, a PCB, an inductive telemetry antenna, and a processing module. The RF antenna is mounted on the PCB. The PCB includes the ground plane of the RF antenna. The ground plane is a continuous conductive layer that defines a plurality of protrusions that define one or more openings. The inductive telemetry antenna is mounted on the PCB over the ground plane. The inductive telemetry antenna comprises a wire that is wound to define a core region of the inductive telemetry antenna. The core region of the inductive telemetry antenna is located over the one or more openings. The processing module is mounted on the PCB and is configured to communicate with a medical device using at least one of the RF antenna and the inductive telemetry antenna.

In some examples according to the present disclosure, a device comprises a first RF antenna, an inductive telemetry antenna, a second RF antenna, a processing module, and a housing. The processing module is configured to communicate with a first medical device using the first RF antenna, communicate with a second medical device using the inductive telemetry antenna, receive first data from a computing device using the second RF antenna, and transmit the first data to at least one of the first medical device and the second medical device. The housing encloses the processing module, the inductive telemetry antenna, and the first and second RF antennas. The housing has a handheld form factor that is configured to be held in a single hand.

The details of one or more examples are set forth in the accompanying drawings and the description below. Other features, objects, and advantages will be apparent from the description and drawings, and from the claims.

BRIEF DESCRIPTION OF THE DRAWINGS

FIGS. 5A-5D show example patterns that may be defined by a ground plane of the RF antenna of a converter device.

DETAILED DESCRIPTION

Figure 1:
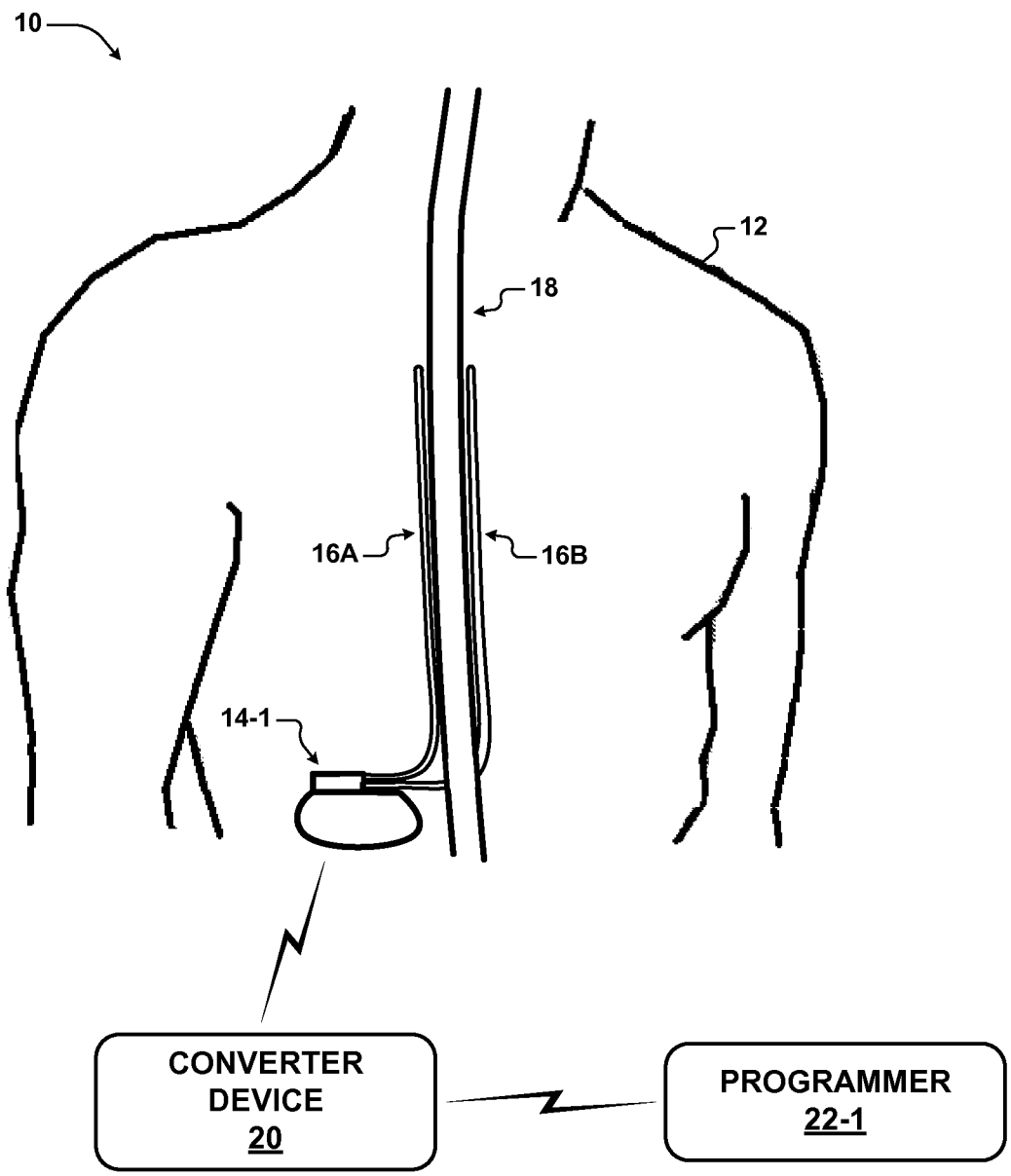
FIG. 1 shows an example implantable medical device (IMD) system that includes an example converter device that communicates with a spinal cord stimulation device and an associated programmer.

Medical devices may include wireless telemetry functionality that provides for wireless communication with a programmer. Medical devices that include wireless telemetry functionality may be implanted in a patient or may be attached externally to the patient. Example devices that include such functionality include, but are not limited to, cardiac electrical therapy devices, neurostimulation devices, and drug pump devices. Cardiac electrical therapy devices may include implantable pacemakers, cardioverters, and/or defibrillators, for example. Neurostimulation devices may be used to stimulate targets that include, but are not limited to, spinal cord targets, deep brain stimulation (DBS) targets, gastric nerves, pelvic nerves, peripheral nerves, and/or a variety of organs, such as the stomach, bladder, or the like. Example drug pump devices may be configured to deliver medication for treatment of chronic pain or diabetes.

A clinician or patient may use a programmer in order to wirelessly communicate with any of the above medical devices. For example, the clinician or patient may use the programmer to program a medical device or retrieve information from a medical device. As used herein, a programmer may refer to any computing device that may typically be used by a clinician or patient to interact with one of the above medical devices. In some examples, the programmer may be a dedicated computing device that is manufactured for use with a particular medical device. In other examples, the programmer may be a general purpose computing device such as a desktop PC, a laptop computer, a tablet computer, or other handheld mobile computing device (e.g., a mobile phone).

Different medical devices may operate using different types of wireless telemetry technologies, and some medical devices may include more than one type of wireless telemetry technology. Different telemetry technologies may communicate in different frequency ranges (i.e., in different frequency bands), include different antenna designs, transmit information at different data rates, and have different clinician usage scenarios (e.g., proximity vs. distance communication). Two different wireless telemetry technologies used in various medical devices include inductive telemetry and RF telemetry.

Inductive telemetry is an example telemetry technology used for communication between a programmer and a medical device, e.g., an implanted medical device with little or tolerable attenuation through body tissue. Robust inductive telemetry devices may communicate over a limited distance, e.g., at a distance of up to approximately 10-100 centimeters. In some examples, a programmer may require close skin contact to communicate with an IMD using inductive telemetry. Programmers that are configured to communicate with IMDs using inductive telemetry may include paddles or wands that are held over the patient's body at the implantation site of the IMD during communication. Because of the relatively limited communication distance, inductive telemetry may also be referred to as "proximity telemetry" in some examples. In general, inductive telemetry may rely on modulation of magnetic field signals to transmit and receive telemetry signals.

RF telemetry is another example telemetry technology used for communication between programmers and medical devices. RF telemetry devices may communicate with medical devices over longer distances than inductive telemetry devices, e.g., approximately 2-5 meters. Because RF telemetry devices may not require close proximity for communication, RF telemetry may also be referred to as "distance telemetry" in some examples. In general, RF telemetry may rely on modulation of electromagnetic field signals to transmit and receive telemetry signals.

RF telemetry and inductive telemetry may operate at different frequency ranges. In some examples, RF telemetry may operate at approximately 401-406 MHz (e.g., in the Medical Implant Communication Service (MICS) band and the Medical Data Service (MEDS) band), or other higher frequency ranges, while inductive telemetry may operate effectively from the Low Frequency (LF) band (e.g., approximately 100 kHz) into medium frequency bands (e.g., approximately 15 MHz), or other lower frequency ranges. RF telemetry generally provides a greater rate of data transfer than inductive telemetry. For example, RF telemetry may provide up to approximately 380 kbps in the MICS band and up to approximately 190 kbps in the MEDS band, while inductive telemetry may provide up to approximately a 4 kbps transfer rate. Additionally, RF telemetry and inductive telemetry antennas included in programmers may have different structures. Antennas used for inductive telemetry may be relatively larger than those used for RF telemetry, and RF telemetry systems may include a ground plane, whereas inductive telemetry antennas may operate without the use of a ground plane.

Programmer and medical device manufacturers have produced, and may continue to produce, a variety of different programmers and medical devices that communicate using different types of wireless telemetry technologies. For example, manufacturers may produce different programmers that are configured to communicate with different types of medical devices, e.g., cardiac electrical therapy devices, neurostimulation devices, etc. Manufacturers may also produce different programmers that include different types of wireless telemetry technologies for communicating with a variety of different medical devices. For example, manufacturers may produce both inductive telemetry and RF telemetry programmers. Additionally, over time, programmers may be updated to include additional or improved hardware and software features.

A converter device of the present disclosure may serve as an intermediate communication device between a variety of different programmers and a variety of different medical devices that use different telemetry technologies. The converter device may include inductive telemetry and RF telemetry functionality for communication with different medical devices. The converter device may also include a different communication technology for communicating with a variety of different programmers. For example, the converter device may include a more widely available communication technology for communicating with the programmer. In some examples, the converter device may include a wireless communication technology for communicating with a programmer, such as Bluetooth (at approximately 2.4 GHz in some examples), or a wireless technology implementing the Institute of Electrical and Electronics Engineers (IEEE) 802.11 standard (e.g., 802.11a/b/g/n). Additionally, or alternatively, the converter device may include a wired communication technology for communicating with a programmer, such as a technology implementing the Universal Serial Bus (USB) standard (e.g., USB 1.0/2.0/3.0). Implementation of such widely available communication technologies in the converter device, for communication with a programmer, may help to ensure future compatibility between current and future programmers and the converter device. For example, implementation of a widely available communication technology may ensure that programmers that are manufactured in the future may be easily integrated with the converter device of the present disclosure, and in turn may ensure that future programmers may be capable of communicating with medical devices having different communication technologies via the converter device.

The converter device of the present disclosure may retrieve data from a medical device using one or more different telemetry technologies (e.g., inductive telemetry and/or RF telemetry) and then transmit the data to a programmer using one of the more widely available communication technologies described above, e.g., Bluetooth, USB, etc. In another example, the converter device of the present disclosure may retrieve data from the programmer using one of the widely available communication technologies, and then transmit the data to a medical device using one or more different telemetry technologies, such as inductive telemetry or RF telemetry. Put another way, the converter device may act as a communication bridge between different medical device communication technologies and a more widely available communication technology.

The converter device of the present disclosure includes components for communicating with medical devices using inductive telemetry. For example, the converter device includes an inductive antenna that is configured to transmit signals to a medical device and receive signals from a medical device using inductive telemetry. The converter device may also include an inductive telemetry module (e.g., electronic hardware, firmware, and/or software) that transmits and receives signals via the inductive antenna.

The converter device of the present disclosure also includes components for communicating with medical devices using RF telemetry. For example, the converter device includes an RF antenna (e.g., a helical antenna) and a ground plane of the RF antenna that are configured to transmit signals to a medical device and receive signals from a medical device using RF telemetry. The converter device may also include an RF telemetry module (e.g., electronics hardware, firmware, and/or software) that transmits and receives signals via the RF antenna.

The converter device of the present disclosure may also include another communication module that is configured to communicate with a programmer using one or more of the more widely available communication technologies described above, such as Bluetooth, IEEE 802.11, and/or USB. The communication module configured to communicate with the programmer using one or more of these communication technologies may be referred to herein as a "programmer communication module."

In some examples, the components of the converter device may be included on a printed circuit board (PCB) and enclosed in a housing. For example, the housing may enclose the PCB, the RF antenna, the inductive antenna, the programmer communication module, and the RF and inductive telemetry modules, along with other components described herein. The housing may have a handheld mobile form factor that the clinician may easily manipulate using only a single hand. The small form factor may also allow for convenient storage of the converter device, e.g., in the clinician's pocket or in a storage cabinet.

The RF antenna included in the converter device may be a helical antenna in some examples. The RF antenna may be connected to (e.g., soldered) to the PCB of the converter device. The PCB includes a ground plane of the RF antenna. The ground plane may be a continuous layer of conductive material, e.g., a continuous copper sheet. As described herein, the continuous layer of conductive material may have a patterned region (e.g., a finger-like pattern) located adjacent to the inductive antenna. The patterned region of the ground plane may define open regions in which portions of the continuous ground plane are absent. Although the patterned region of the ground plane may define such open regions, the ground plane as a whole may be still provide adequate RF telemetry performance. In other words, the patterning of the ground plane in the region adjacent to the inductive telemetry antenna may not appreciably affect the performance of the RF telemetry system.

The continuous ground plane may cover a substantial portion of a PCB layer, which may help ensure reliable performance of the RF antenna. As described hereinafter, the inductive antenna may be mounted to the PCB over top of the ground plane. In other words, the ground plane may extend under the inductive antenna. The portion of the ground plane located under the inductive antenna may not be a completely solid ground plane, but instead may be patterned to define open regions, i.e., regions that do not include portions of the continuous ground plane. In one example, the pattern under the inductive antenna defines a plurality of projections (e.g., a finger-like pattern) that define open regions between the projections.

In some examples, a ground plane located under a core of an inductive antenna may cause a decrease in the transmission performance of the inductive antenna, e.g., due to eddy currents that may arise in the ground plane. However, in the converter device of the present disclosure, the open region(s) under the inductive antenna (e.g., under the core of the inductive antenna) may be configured to allow for proper operation of the inductive antenna while at the same time providing a proper ground plane for the RF antenna that does not substantially degrade RF communication performance. In other words, even though the inductive antenna is placed over a ground plane in the converter device, the patterned region of the ground plane located under the inductive antenna may be configured (i.e., shaped) to enable high performance of the inductive antenna, e.g., by breaking up eddy currents, without reducing RF performance.

In some examples, the one or more open regions under the core region of the inductive antenna may comprise approximately half of the area under the core region, and the ground plane may comprise the remaining area under the core region. In other examples, the one or more open regions under the core region of the inductive antenna may comprise approximately seventy percent of the area under the core region, and the ground plane may comprise the remaining thirty percent of the area under the core region. The percentage of the area under the core region that comprises ground plane, and the percentage of the area under the core region that comprises open regions may depend on the desired performance of the different telemetry schemes. For example, a larger percentage of ground plane may tend to improve RF communication, but may tend to degrade inductive telemetry performance.

The inductive antenna may comprise a support structure and a wire. The support structure may house the wire, and the wire may be wound one or more times around the support structure. The wire may be wound around the support structure one or more times such that a center region is defined within a perimeter created by the wire and the support structure. The center region defined by the wire and supporting structure may be referred to as a "core" in some examples. In the case of the inductive antenna of the present disclosure, the core of the inductive antenna may be an air core. The inductive antenna (i.e., support structure and wire) described in the present disclosure may define a substantially rectangular shape. The substantially rectangular shape may be described as a rounded rectangle, or as a rectangle having rounded corners. In other words, the support structure of the inductive antenna may have rounded rectangle shape, and the wire which is supported by the support structure, and housed by the support structure, may have a rounded rectangular shape when wound around the support structure. The rounded rectangular shape may resemble a racing track, and accordingly, in some examples, the inductive antenna may be referred to as a "racetrack antenna."

The inductive antenna may be connected to the PCB and arranged adjacent to the ground plane. For example, the support structure may be connected to the PCB such that the rectangular shape of the support structure overlays the PCB. In other words, the entire rectangular shape of the support structure may abut, or nearly abut, the PCB such that the PCB and patterned ground plane may be viewed through the opening (i.e., core) defined by the support structure, assuming the ground plane is visible on top of the PCB and not embedded in lower layers of the PCB. For example, the inductive antenna may be located adjacent to the ground plane such that the inductive antenna is approximately the same distance from the ground plane over the entire perimeter of the support structure. In some examples, the orientation of the inductive antenna to the PCB may be described by visualizing an axis of the inductive antenna. The wire of the inductive antenna may be visualized as circumscribing the axis of the inductive antenna a plurality of times, the axis forming a right angle to the rectangular profile of the inductive antenna and also intersecting the ground plane at a right angle.

The converter device may be used by a clinician or patient in a variety of different ways. In some usage scenarios, a clinician may first initiate communication between the programmer and the converter device, and then initiate communication between the medical device and the converter device. In other usage scenarios, a clinician may first initiate communication between the medical device and the converter device, and then initiate communication between the programmer and the converter devices. Regardless of the order in which communication may be initiated, after initiation, the programmer may communicate with the medical device through the converter device. In examples where the converter device may communicate with the medical device at a distance, the clinician may conveniently locate the converter device next to the patient, or at a distance from the patient, while using the programmer to communicate with the medical device via the converter device.

In one usage scenario, the clinician may use the inductive antenna to exchange a security key with a medical device in close proximity. The converter may then use the key to initiate a secure RF communication between the converter and the medical device. This usage scenario of the converter device may allow the clinician to conveniently use a single handheld device to both initiate a secure RF communication and then subsequently communicate with the medical device using the secure RF communication from a distance.

In some examples, the converter device may include an additional RF antenna for communication with a medical device. The additional RF antenna may be added to the PCB of the converter device. In these examples, both of the RF antennas may share the ground plane. In examples where the converter device includes multiple RF antennas, the converter device may selectively switch between the multiple RF antennas in order to select the RF antenna that provides the most accurate communication with the medical device. For example, upon detection of an error during communication using one of the RF antennas, the converter device may switch to the other RF antenna in an attempt to bypass the error.

Figure 2:
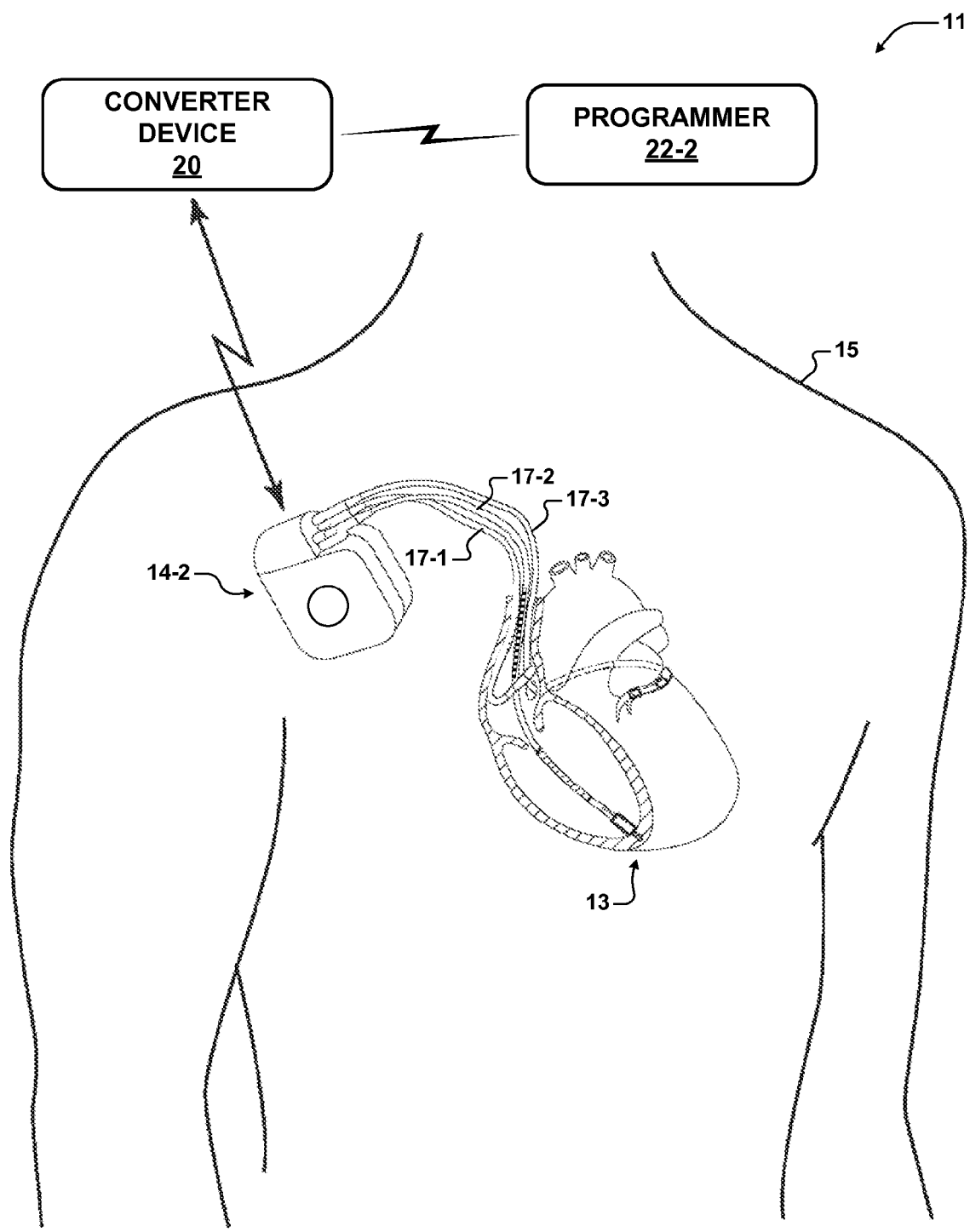
FIG. 2 shows another example IMD system that includes a converter device that communicates with a cardiac electrical therapy device and an associated programmer.

The converter device of the present disclosure may be configured to communicate with a variety of different types of medical devices and programmers. FIGS. 1-2 show example medical devices and programmers with which the converter device may communicate. FIG. 1 shows an example IMD system that includes an example converter device 20 that communicates with a spinal cord stimulation device 14-1 and a programmer 22-1 associated with spinal cord stimulation device 14-1. FIG. 2 shows another example IMD system that includes converter device 20 that communicates with a cardiac electrical therapy device 14-2 and an associated programmer 22-2. FIGS. 1-2 are meant to show that an example converter device 20 may communicate with different medical devices and programmers associated with those medical devices. Although converter device 20 is illustrated as communicating with a spinal cord stimulation device 14-1, a cardiac electrical therapy device 14-2, and associated programmers 22-1, 22-2, it is contemplated that converter device 20 of the present disclosure may be configured to communicate with other medical devices, both external and implantable, and other programmers. A medical device with which converter device 20 may communicate may be referred to generally herein as "medical device 14." A programmer with which converter device 20 may communicate may be referred to generally herein as "programmer 22."

FIG. 1 is a diagram of an example system 10 for providing electrical stimulation therapy to a patient 12 using an implantable electrical stimulator. In the example of FIG. 1, system 10 includes an implantable electrical stimulator 14-1 (hereinafter "stimulator 14-1"), programmer 22-1, and converter device 20. Stimulator 14-1 may be implanted within patient 12. In other examples, stimulator 14-1 may be an external stimulator, e.g., an external neural stimulator, which may be used on a trial basis with percutaneous leads to test stimulation on patient 12. Programmer 22-1 may communicate with stimulator 14-1 via converter device 20.

As shown in FIG. 1, stimulator 14-1 may be coupled to electrical leads 16A and 16B (collectively "leads 16"). Leads 16 include electrodes (not shown) that deliver the electrical stimulation therapy to patient 12. In some implementations, stimulator 14-1 may include electrodes on the housing of stimulator 14-1 in addition to electrodes on leads 16. In the example of FIG. 1, leads 16 are implanted along the length of spinal cord 18 such that electrical stimulation from leads 16 affects spinal cord 18. In other examples, one or more of leads 16 may be implanted so that electrodes are placed at target locations adjacent deep brain stimulation (DBS) targets, gastric nerves, pelvic nerves, peripheral nerves, and/or a variety of organs such as the heart, stomach, bladder, or the like. Although two leads 16 are shown in FIG. 1, in other implementations, system 10 may include more or less than two leads 16 implanted within patient 12.

Stimulator 14-1 delivers electrical stimulation according to a set of stimulation parameters. Stimulation parameters may include voltage or current pulse amplitudes, pulse widths, pulse rates, electrode combination, and electrode polarity. A combination of the stimulation parameters may be referred to as a "stimulation program." A stimulation program, or multiple stimulation programs, may be stored in stimulator 14-1 and/or programmer 22-1. Stimulator 14-1 may provide stimulation according to one or more stimulation programs. For example, stimulator 14-1 may deliver pulses according to the one or more stimulation programs by sequentially delivering pulses from each of the programs, e.g., on a time-interleaved basis.

Using programmer 22-1, a user (e.g., a clinician or patient 12) may create one or more customized stimulation programs that define the electrical stimulation delivered to patient 12 by stimulator 14-1. Programmer 22-1 may transmit the stimulation programs created by the user to stimulator 14-1 via converter device 20. For example, Programmer 22-1 may transmit the stimulation programs to converter device 20, then converter device 20 may transmit the stimulation programs to stimulator 14-1. Stimulator 14-1 subsequently generates and delivers electrical stimulation therapy according to the stimulation programs created by the user to treat a variety of patient conditions, as described above. The user may use programmer 22-1 to select values for a number of stimulation parameters in order to define the electrical stimulation therapy to be delivered by stimulator 14-1. For example, the user may select stimulation parameters that define a current or voltage amplitude of electrical pulses delivered by the stimulator, a pulse rate, a pulse width, and a configuration of electrodes that deliver the pulses, e.g., in terms of selected electrodes and associated polarities.

Converter device 20 may also receive data from stimulator 14-1 and transfer the received data to programmer 22-1 using wireless communication. Example data that may be collected by stimulator 14-1 and transmitted to programmer 22-1 via converter device 20 may include a status of the battery, electrical operational status, lead impedance, and sensed physiological signals. Stimulator 14-1 and converter device 20 may communicate using RF telemetry and/or inductive telemetry, and converter device 20 and programmer 22-1 may communicate using wired and/or wireless communication, such as Bluetooth, IEEE 802.11a/b/g/n, and/or USB.

FIG. 2 shows an example system 11 that may be used to diagnose conditions of and provide therapy to a heart 13 of a patient 15. System 11 includes an IMD 14-2. For example, IMD 14-2 may be an implantable pacemaker, cardioverter, and/or defibrillator that monitors electrical activity of heart 13 and provides electrical stimulation to heart 13.

IMD 14-2 includes leads 17-1, 17-2, 17-3 (collectively "leads 17") that extend into heart 13. IMD 14-2 may sense electrical activity of heart 13 and/or deliver electrical stimulation (e.g., pacing pulses and/or arrhythmia therapy) to heart 13 via electrodes on leads 17 or on the housing of IMD 14-2, e.g., using a unipolar or bipolar combination of electrodes. For example, IMD 14-2 may detect an arrhythmia of heart 13, such as ventricular tachyarrhythmia (VT) or ventricular fibrillation (VF), and deliver antitachycardia pacing (ATP) therapy, cardioversion, or defibrillation therapy to heart 13 in response to the detection of VT/VF. IMD 14-2 may enclose an electrical sensing module that monitors electrical activity of heart 13, and may also enclose a signal generator module that generates therapeutic stimulation, such as cardiac pacing pulses, ATP therapy, cardioversion therapy, and/or defibrillation therapy.

IMD 14-2 and programmer 22-2 may wirelessly communicate with one another via converter device 20. IMD 14-2 and converter device 20 may communicate using RF telemetry and/or inductive telemetry, and converter device 20 and programmer 22-2 may communicate using wired and/or wireless communication, such as Bluetooth and/or USB. Converter device 20 may retrieve data from IMD 14-2 and then transmit the retrieved data to programmer 22-2. Additionally, programmer 22-2 may send data to converter device 20 to program into IMD 14-2, then converter device 20 may send the received data to IMD 14-2 to program IMD 14-2.

Data retrieved from IMD 14-2 using converter device 20 may include cardiac electrograms (EGMs) stored by IMD 14-2 that indicate electrical activity of heart 13 and marker channel data that indicates the occurrence and timing of sensing, diagnosis, and therapy events associated with IMD 14-2. Additionally, data may include information regarding the performance or integrity of IMD 14-2 or other components of diagnostic system 11, such as leads 17. Data transferred from programmer 22-2 to converter device 20, and then from converter device 20 to IMD 14-2, may include parameters to be programmed into IMD 14-2, for example.

Figure 3:
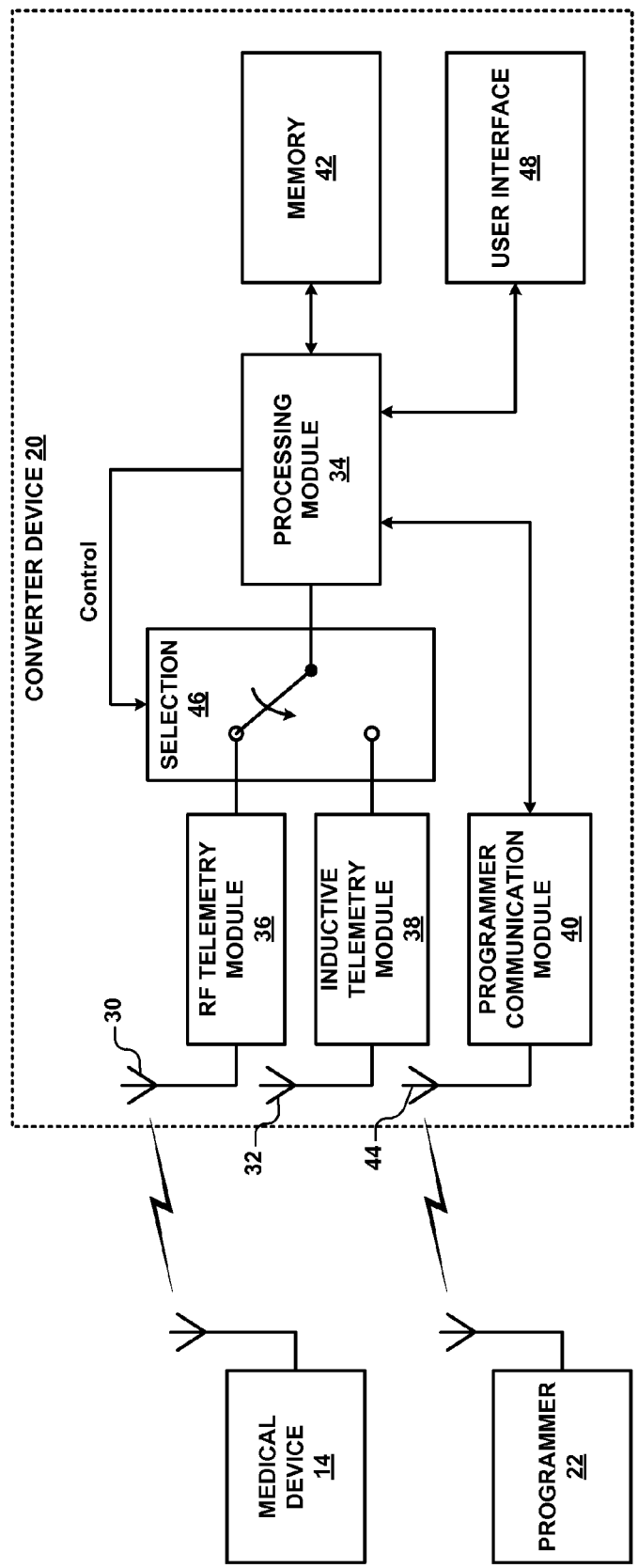
FIG. 3 is a functional block diagram of an example converter device of the present disclosure.

FIG. 3 is a functional block diagram of an example converter device 20 of the present disclosure. Converter device 20 may serve as an intermediate communication device between a programmer 22 and a medical device 14. Programmer 22 may generally represent any computing device that may typically be used by a clinician or patient to interact with a medical device. In some examples, programmer 22 may be a dedicated computing device that is manufactured for use with a particular medical device. In other examples, programmer 22 may be a general purpose computing device such as a desktop PC, a laptop computer, a tablet computer, or other handheld mobile computing device (e.g., a mobile phone). Medical device 14 may generally represent any medical device that includes wireless communication functionality, such as a cardiac electrical therapy device, a neurostimulation device, or a drug pump device. Medical device 14 may be configured for implantation in a patient or external attachment to the patient.

In general, converter device 20 may retrieve data from medical device 14 using either inductive telemetry communication or RF telemetry communication, and then transmit the data to programmer 22 using one or more of the more widely available communication technologies described above, such as Bluetooth, USB, etc. Additionally, converter device 20 may retrieve data from programmer 22 and then transmit the data to medical device 14 using either inductive telemetry communication or RF telemetry communication.

Converter device 20 includes an RF antenna 30 and an inductive antenna 32. RF antenna 30 may be configured to transmit signals to medical device 14 and receive signals from medical device 14 using RF telemetry. RF antenna 30 may be configured to operate in a high frequency, RF band, such as, for example, the MICS/MEDS band, while inductive antenna 32 may be configured to operate at a lower frequency band of approximately 100 kHz to approximately 15 MHz, or other lower frequency ranges. In some examples, RF antenna 30 may represent a helical antenna and a ground plane of the helical antenna which are configured to receive and transmit signals using RF telemetry. Inductive antenna 32 is configured to transmit signals to medical device 14 and receive signals from medical device 14 using inductive telemetry. As described herein, inductive antenna 32 may be mounted over the ground plane of RF antenna 30, and the portion of the ground plane located under inductive antenna 32 may be patterned to define one or more open regions that underlie inductive antenna 32.

Converter device 20 includes a processing module 34, an RF telemetry module 36, an inductive telemetry module 38, and a programmer communication module 40. Modules included in converter device 20 represent functionality that may be included in converter device 20 of the present disclosure. Modules of the present disclosure may include any discrete and/or integrated electronic circuit components that implement analog and/or digital circuits capable of producing the functions attributed to the modules herein. For example, the modules may include analog circuits, e.g., amplification circuits, filtering circuits, and/or other signal conditioning circuits. The modules may also include digital circuits, e.g., combinational or sequential logic circuits, memory devices, etc. Memory may include any volatile, non-volatile, magnetic, or electrical media, such as a random access memory (RAM), read-only memory (ROM), non-volatile RAM (NVRAM), electrically-erasable programmable ROM (EEPROM), Flash memory, or any other memory device. Furthermore, memory may include instructions that, when executed by one or more processing circuits, cause the modules to perform various functions attributed to the modules herein.

The functions attributed to the modules herein may be embodied as one or more processors, hardware, firmware, software, or any combination thereof. Depiction of different features as modules is intended to highlight different functional aspects and does not necessarily imply that such modules must be realized by separate hardware or software components. Rather, functionality associated with one or more modules may be performed by separate hardware or software components, or integrated within common or separate hardware or software components.

Processing module 34 may control the general functions of converter device 20. Memory 42 may include instructions that, when executed by processing module 34, cause processing module 34 to perform various functions attributed to processing module 34 described herein. RF telemetry module 36 may transmit and receive data via RF antenna 30. Processing module 34 may transmit data to medical device 14 and receive data from medical device 14 using RF telemetry module 36. Inductive telemetry module 38 may transmit and receive data via inductive antenna 32. Processing module 34 may transmit data to medical device 14 and receive data from medical device 14 using inductive telemetry module 38. Programmer communication module 40 may communicate with programmer 22. As illustrated in FIG. 3, programmer communication module 40 may wirelessly communicate with programmer 22 using antenna 44. For example, programmer communication module 40 may wirelessly communicate with programmer 22 using Bluetooth and/or IEEE 802.11a/b/g/n. In other examples, programmer communication module 40 may communicate with programmer 22 using a wired communication technology, such as USB. Wired communication may be used instead of, or in addition to, communicating with programmer 22 using a wireless communication technology as illustrated in FIG. 3. Processing module 34 may communicate with programmer 22 via programmer communication module 40.

Processing module 34 may communicate with medical device 14 via RF telemetry module 36 and/or inductive telemetry module 38. In some examples, processing module 34 may select which of RF telemetry module 36 and inductive telemetry module 38 to use for communication with medical device 14. The selection of either RF communication or inductive communication may be represented by selection module 46. In the example of FIG. 3, processing module 34 may control selection module 46 to connect either RF telemetry module 36 to processing module 34 or inductive telemetry module 38 to processing module 34. Processing module 34 may control selection module 46 to connect RF telemetry module 36 to processing module 34 in order to communicate with medical device 14 using RF telemetry. Processing module 34 may control selection module 46 to connect to inductive telemetry module 38 in order to communicate with medical device 14 using inductive telemetry. Although selection between either communication using RF telemetry or inductive telemetry is illustrated in FIG. 3, in some examples, it is contemplated that processing module 34 may not discretely select either RF telemetry communication or inductive communication, but instead, processing module 34 may communicate using both RF telemetry module 36 and inductive telemetry module 38 simultaneously.

Converter device 20 may include a user interface 48 with which the user may interact in order to control converter device 20. User interface 48 may represent a variety of different input and output functionalities included in converter device 20. For example, user interface 48 may include a display. Processing module 34 may output information to the display of user interface 48. User interface 48 may also include controls, such as buttons, knobs, a touch screen, etc. Processing module 34 may receive input from the controls of user interface 48.

Processing module 34 may execute an application stored in memory 42. The application stored in memory 42 and executed by processing module 34 may define how processing module 34 controls the various functions of converter device 20. For example, the application may define how processing module 34 displays information on the display of user interface 48 and how processing module 34 responds to inputs from user interface 48. Additionally, the application executed by processing module 34 may define how processing module 34 initiates communication with programmer 22 via programmer communication module 40, how processing module 34 initiates communication with medical device 14 via RF telemetry module 36 and/or inductive telemetry module 38, and how processing module 34 transfers data between medical device 14 and programmer 22.

The user may interact with user interface 48 in order to initiate communication between medical device 14 and converter device 20 via RF telemetry module 36 and/or inductive telemetry module 38. The user may also interact with user interface 48 to initiate communication between programmer 22 and converter device 20 via programmer communication module 40. After initiation of communication, converter device 20 may receive data from programmer 22 using programmer communication module 40, and processing module 34 may send the data to medical device 14 using RF telemetry module 36 and/or inductive telemetry module 38. Similarly, after initiation of communication, converter device 20 may receive data from medical device 14 using RF telemetry module 36 and/or inductive telemetry module 38, and processing module 34 may send the received data to programmer 22 using programmer communication module 40. In some examples, converter device 20 may be configured to be controlled by programmer 22. In these examples, converter device 20 may include a minimalistic user interface.

Figure 6C:
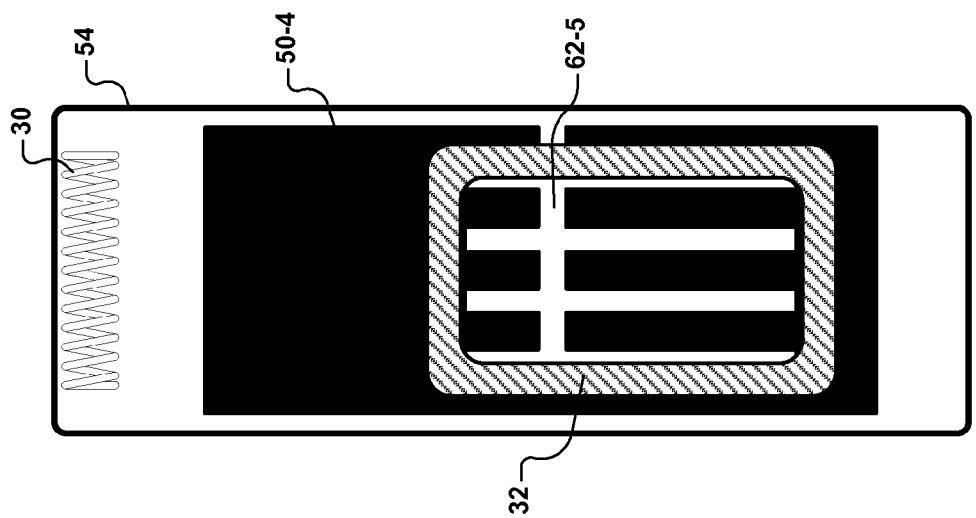
FIGS. 6A-6C show the inclusion of the ground plane patterns of FIGS. 5B-5D on a PCB.
Figure 6B:
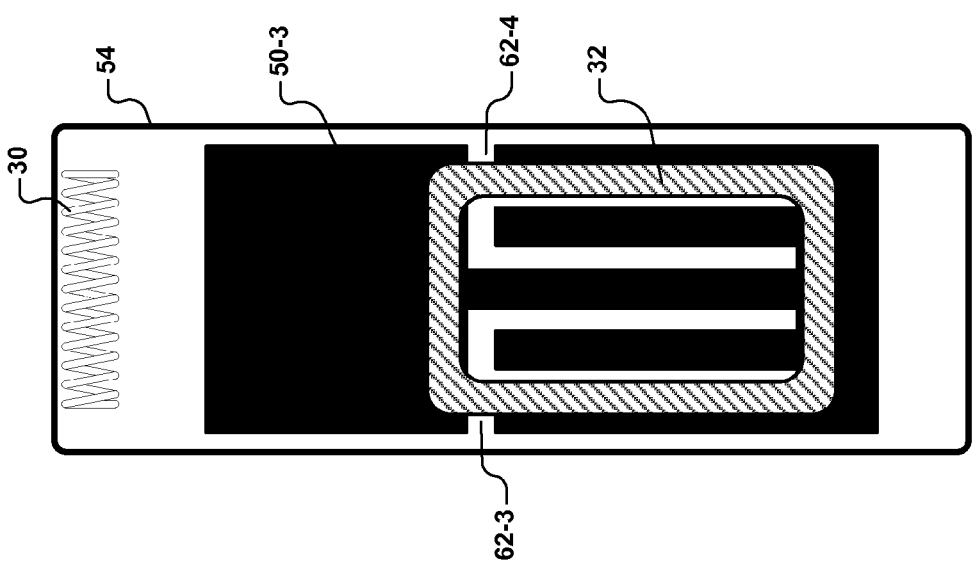
Figure 6A:
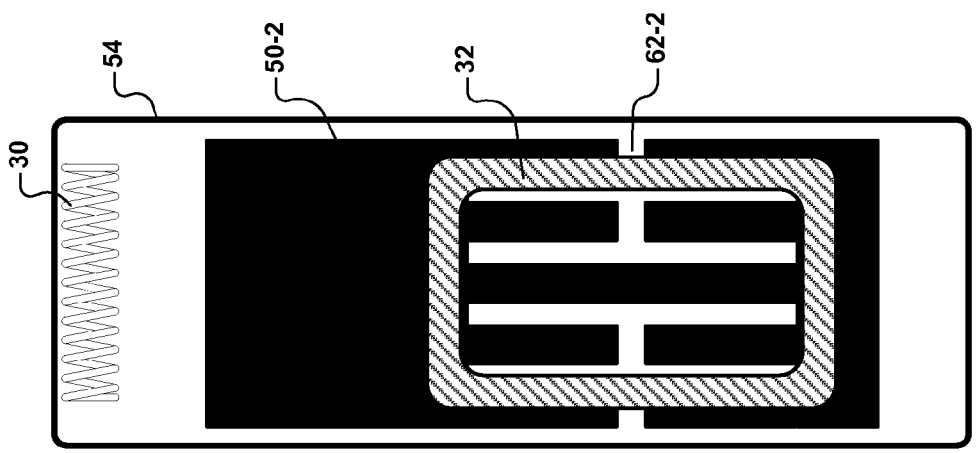
Figure 7:
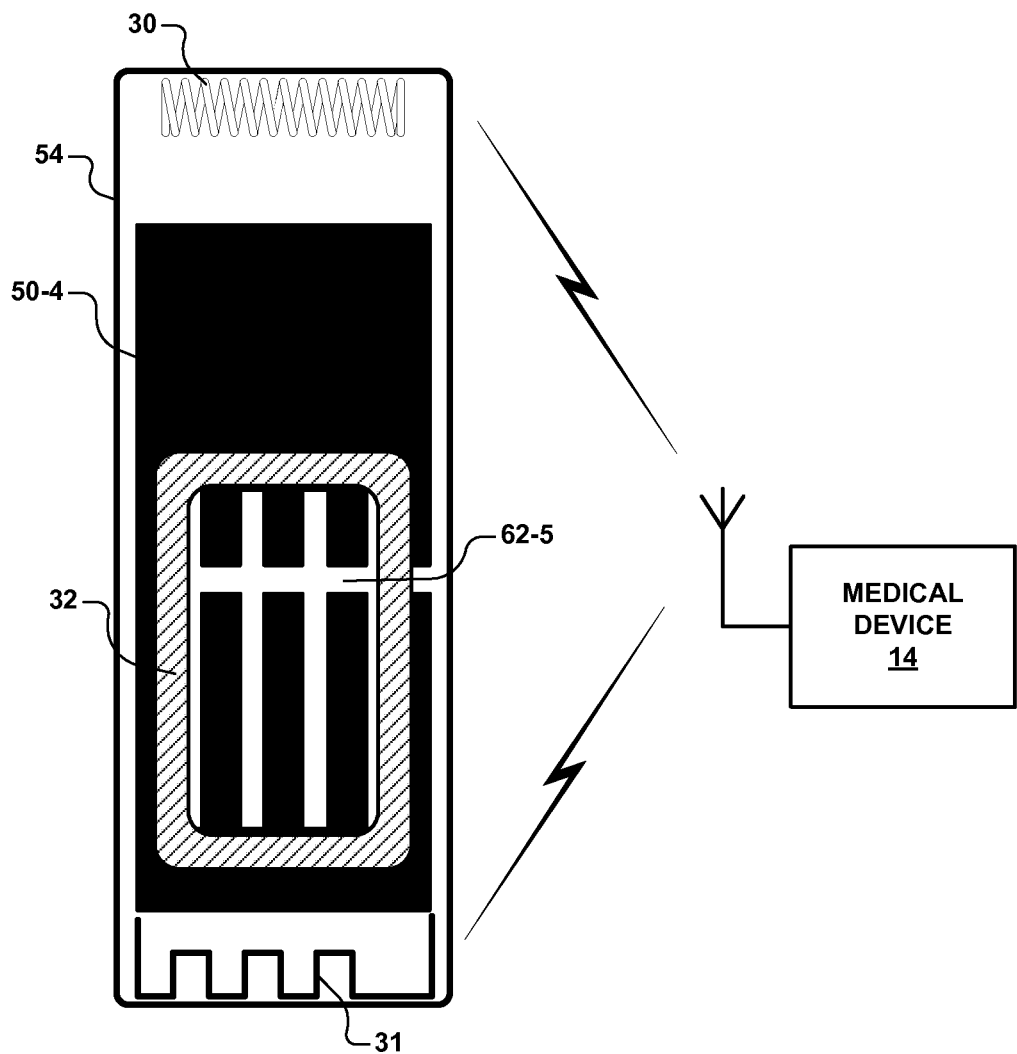
FIG. 7 shows the inclusion of an additional RF antenna in a converter device.

Example layouts of components within converter device 20 are now described with respect to FIGS. 4-7. FIGS. 4-7 show some example arrangements of RF antenna 30, ground plane (e.g., 50-1, 50-2, 50-3, 50-4) of RF antenna 30, and inductive antenna 32 on a PCB 54 of converter device 20. FIGS. 5A-5D show example patterns that may be defined by a ground plane (e.g., 50-1, 50-2, 50-3, 50-4). FIGS. 6A-6C show the inclusion of the ground plane patterns of FIGS. 5B-5D on PCB 54. FIG. 7 shows the inclusion of an additional RF antenna 31 on PCB 54 that may be used to communicate with medical device 14. FIGS. 4-7 generally illustrate the layout of antennas 30, 32 and example ground planes 50-1, 50-2, 50-3, 50-4 on PCB 54, and may not illustrate all additional electronic components included in converter device 20 (e.g., modules 34, 36, 38, 40, 46), electrical interconnects, and other mechanical components that may be included in converter device 20. The additional electronic components, electrical interconnects, and other mechanical components are omitted from FIGS. 4-7 in order to provide a clearer view of the arrangement of antennas 30, 32 and ground planes 50-1, 50-2, 50-3, 50-4 of converter device 20.

Figure 4C:
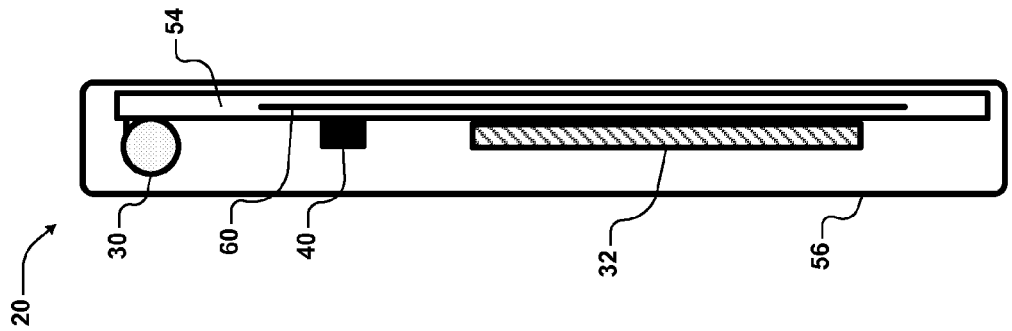
FIGS. 4A-4C show example arrangements of a radio-frequency (RF) antenna, a ground plane of the RF antenna, and an inductive antenna on a printed circuit board (PCB) of a converter device.
Figure 4B:
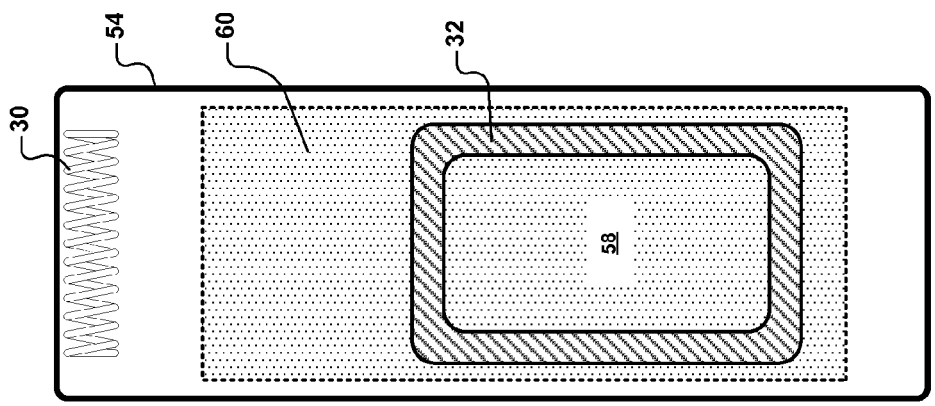
Figure 4A:
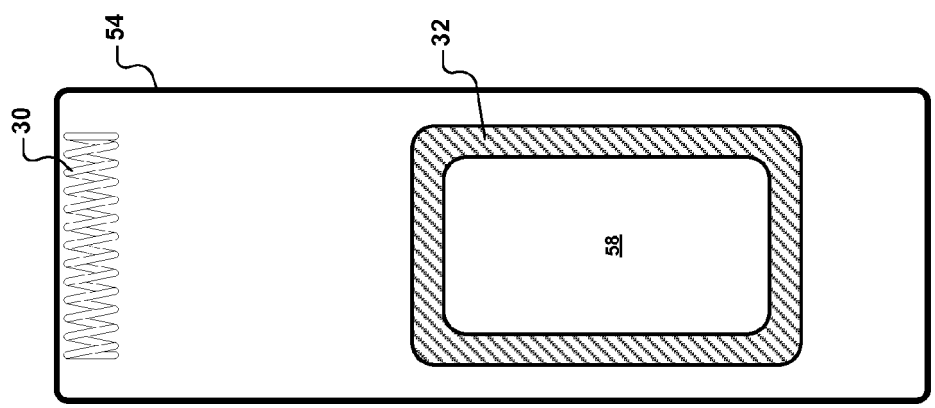

FIG. 4A shows an example arrangement of RF antenna 30 and inductive antenna 32 on PCB 54. RF antenna 30 may be a helical antenna that is mounted to PCB 54. For example, both ends of RF antenna 30 may be soldered to PCB 54. In some examples, one end of RF antenna 30 may be soldered to PCB 54, but not connected to other components on PCB 54. The other end of RF antenna 30 may be connected to RF telemetry module 36 via a transmission line on PCB 54. Although RF antenna 30 may be a helical antenna in some examples, it is contemplated that an RF antenna may include other antenna geometries and configurations. For example, RF antenna 30 may include a planar inverted F antenna (PIFA), an inverted F antenna (IFA), a meandering antenna, and/or a folded monopole antenna geometry.

Inductive antenna 32 may also be mounted on PCB 54. As illustrated herein, RF antenna 30 and inductive antenna 32 are mounted on the same side of PCB 54. In other examples, RF antenna 30 and inductive antenna 32 may be mounted on different sides of PCB 54. Although RF antenna 30 and inductive antenna 32 are illustrated and described herein as being mounted on PCB 54, in other examples, antennas 30, 32 may be mounted in other places within the housing, or outside of the housing, of converter device 20 and connected via lead wires to electrical components of converter device 20. Mounting RF antenna 30 on a different side of PCB 54 as inductive antenna 32, or mounting antennas 30, 32 off of PCB 54, may not use the space within the housing of converter device 20 as efficiently as mounting of antennas 30, 32 on the same side of PCB 54, and therefore, such mounting may tend to increase the thickness of converter device 20 as a whole.

FIG. 4C shows a side view of converter device 20 having an example housing 56 that encloses PCB 54, RF antenna 30, ground plane (e.g., 50-1, 50-2, 50-3, 50-4), inductive antenna 32, and other electronic and mechanical components included in converter device 20 described herein. Housing 56 may have a handheld mobile form factor that a user may easily manipulate using only a single hand. The small form factor may allow for convenient storage of converter device 20, e.g., in a storage cabinet, drawer, or in the user's pocket. In some examples, the small form factor may be approximately 6"×2"×0.75". In other examples, the small form factor may be approximately 5"×2"×1". Other form factors, e.g., similar to that of a mobile phone, are also contemplated.

Inductive antenna 32 may include a support structure and a wire that is wound around the support structure to define an open center region 58 (i.e., a core region 58). The entire shaded region of inductive antenna 32 as illustrated in FIGS. 4-7 may represent the support structure of inductive antenna 32. The wire of inductive antenna 32 is not visible in FIGS. 4-7 because the wire may be housed within the support structure of inductive antenna 32. Inductive antenna (i.e., support structure and wire) illustrated in FIGS. 4-7 defines a substantially rectangular shape. The substantially rectangular shape may be described as a rounded rectangle, or as a rectangle having rounded corners. Although inductive antenna 32 is illustrated herein as having has a substantially rectangular shape, inductive antenna 32 may also have other shapes. For example, inductive antenna 32 may have a circular or oval shape in other examples.

FIG. 4B shows a shaded region 60 of PCB 54 in which a ground plane of RF antenna 30 may be fabricated. Shaded region 60 covers most of the usable area of PCB 54, and, in a sense, may represent nearly the largest single ground plane that may be achievable on a single layer of PCB 54, unless the ground plane were extended completely to the edges of PCB 54 in all directions. As described hereinafter, a large ground plane area may tend to provide a better RF ground than a smaller ground plane area. And therefore, from the perspective of RF antenna performance, a large ground plane within converter device 20 may be preferable to a smaller ground plane.

FIG. 4C shows an example programmer communication module 40 that may also include an RF antenna (not shown) for wireless communication with programmer 22. Programmer communication module 40 may implement one or more of a variety of different technologies for wireless communication with programmer 22. For example, programmer communication module 40 may include an antenna and circuitry for providing Bluetooth communication with programmer 22. In other examples, programmer communication module 40 may include alternative, or additional, wireless communication technologies, such as IEEE 802.11a/b/g/n. Although not illustrated herein, PCB 54 may also include connectors and circuitry for implementing one or more wired communication technologies for communicating with programmer 22, such as USB. The profile thickness of shaded region 60 is also illustrated in FIG. 4C. Shaded region 60 in FIG. 4C may generally illustrate where an RF ground plane (e.g., 50-1, 50-2, 50-3, 50-4) may be included in PCB 54. In some examples, a ground plane may be deposited on the top or bottom layer of PCB 54. In other examples, a ground plane may be deposited on an inner layer of PCB 54. In some examples, a ground plane may be deposited on multiple layers of PCB 54 and interconnected between the layers, e.g., using conductive vias.

A variety of different ground planes that may be fabricated in shaded region 60 are now described with respect to FIGS. 5A-5D. FIG. 5A shows a solid ground plane 50-1 that does not include open regions (e.g., 62-1, 62-2, 62-3). Although a large area ground plane may be preferable from the perspective of RF antenna performance, the performance of inductive antenna 32 may suffer when a solid ground plane (i.e., without open regions) is located under core region 58 of inductive antenna 32. In some examples, performance of inductive antenna 32 may suffer due to eddy currents that may be generated in ground plane 50-1 during operation of inductive antenna 32. FIGS. 5B-5D show example patterned ground planes 50-2, 50-3, 50-4 that may be used in place of solid ground plane 50-1. Patterned ground planes 50-2, 50-3, 50-4, which define open regions 62-1, 62-2, 62-3, 62-4, 62-5 under core region 58, may provide for both high quality RF performance and high quality inductive antenna performance.

Patterned ground planes 50-2, 50-3, 50-4 include open regions 62-1, 62-2, 62-3, 62-4, 62-5 (collectively "open regions 62"). Any of patterned ground planes 50-2, 50-3, 50-4 may be fabricated in shaded region 60. FIGS. 6A-6C illustrate example PCB 54 that includes ground planes 50-2, 50-3, 50-4 fabricated in shaded region 60. General characteristics that may be applicable to each of patterned ground planes 50-2, 50-3, 50-4 are now described with respect to patterned ground plane 50-2.

Ground plane 50-2 of RF antenna 30 may be fabricated on PCB 54. For example, patterned ground plane 50-2 may be deposited on either side of PCB 54 or within one or more layers of PCB 54. Patterned ground plane 50-2 may be a continuous layer of conductive material, e.g., a continuous copper sheet. Patterned ground plane 50-2 may be continuous in that patterned ground plane 50-2 forms a continuous conductor such that any two points on patterned ground plane 50-2 may be electrically connected by a low resistance path through patterned ground plane 50-2.

Patterned ground plane 50-2 may be described as including protrusions (e.g., 64-1, 64-2), or finger-like projections, that define one or more open regions (e.g., 62-1, 62-2) in patterned ground plane 50-2. Two open regions may be defined in patterned ground planes 50-2, 50-3 (e.g., 62-1, 62-2, 62-3, 62-4), while one open region 62-5 may be defined in patterned ground plane 50-4. In one respect, open regions 62-1, 62-2 in patterned ground plane 50-2 may also be described as regions under inductive antenna 32 in which conductive material is absent. Although protrusions (e.g., 64-1, 64-2) and open regions (e.g., 62-1, 62-2, 62-3, 62-4, 62-5) are illustrated as having straight edges, in some examples, protrusions and open regions may be defined by curved edges. Although patterned ground plane 50-2 defines openings 62-1, 62-2, patterned ground plane 50-2 may still cover a substantial portion of a layer of PCB 54, which may help ensure reliable RF performance.

FIGS. 6A-6C show inductive antenna 32 mounted onto PCB 54 over patterned ground planes 50-2, 50-3, 50-4. With respect to FIG. 6A, inductive antenna 32 is mounted over patterned ground plane 50-2 such that core region 58 of inductive antenna 32 is located over open regions 62-1, 62-2 of patterned ground plane 50-2. In other words, patterned ground plane 50-2 may extend under inductive antenna 32, and portions of patterned ground plane 50-2 defining open regions 62-1, 62-2 in patterned ground plane 50-2 may extend under core region 58 of inductive antenna 32. Portions of patterned ground plane 50-2 that do not extend under core region 58 may be solid, i.e., may not include openings.

In some examples, open regions 62-1, 62-2 under core region 58 of inductive antenna 32 may comprise approximately seventy percent or less of the area under core region 58, and ground plane 50-2 may comprise the remaining area under core region 58. In other words, ground plane 50-2 may comprise approximately thirty percent or more of the area under core region 58. For example, ground plane 50-2 may comprise approximately half of the area under core region 58. The percentage of the area under core region 58 that comprises ground plane 50-2, and the percentage of the area under core region 58 that comprises open regions 62-1, 62-2 may depend on the desired performance of the different telemetry schemes. For example, a larger percentage of ground plane may tend to improve RF communication, but may tend to degrade proximal telemetry performance.

The support structure of inductive antenna 32 may be connected to PCB 54 such that the rectangular shape of the support structure overlays PCB 54. In other words, the entire rectangular shape of the support structure may abut, or nearly abut, PCB 54 such that PCB 54 and patterned ground plane 50-2 may be viewed through core region 58 defined by the support structure and the wire that is wound around the support structure, assuming patterned ground plane 50-2 is visible on the same side of PCB 54 to which inductive antenna 32 is mounted. The orientation of inductive antenna 32 relative to patterned ground plane 50-2 may also be described in terms of the wire of inductive antenna 32. For example, the wire winding of inductive antenna 32 may be located adjacent to patterned ground plane 50-2 such that the wire winding is approximately the same distance from patterned ground plane 50-2 over the entire perimeter of the wire winding. The orientation of the wire winding relative to patterned ground plane 50-2 may also be described by first visualizing an axis of the wire winding around which the wire winding is wrapped. Such an axis may form a right angle to a plane including the wire winding and may also intersect patterned ground plane 50-2 at a right angle.

Even though inductive antenna 32 is placed over patterned ground plane 50-2, which may be a continuous conductor, inductive telemetry performance may not suffer since open regions 62-1, 62-2 may serve to break up patterned ground plane 50-2 from the viewpoint of inductive antenna 32. The breaking up of patterned ground plane 50-2 from the viewpoint of inductive antenna 32 may serve to reduce or eliminate the effects that would be experienced by inductive antenna 32 had it been placed over a solid ground plane. For example, breaking up of patterned ground plane 50-2 may reduce eddy currents caused by operation of inductive antenna 32.

Referring now to FIG. 7, converter device 20 may include an additional RF antenna 31. RF antenna 31 may be included on PCB 54. RF antenna 31, as illustrated in FIG. 7, may be a serpentine antenna trace that is included on a layer of PCB 54. Although RF antenna 31 is illustrated as a serpentine trace included on a layer of PCB 54, it is contemplated that RF antenna 31 may be implemented in a variety of different ways, e.g., as a helical antenna mounted to PCB 54, similar to RF antenna 30.

RF antenna 31 may share patterned ground plane 50-4 and may be configured to operate at similar frequency ranges (e.g. in the MICS/MEDS band) as RF antenna 30. RF antenna 31 may connect to RF telemetry module 36 via a transmission line. In examples where RF antenna 30 and RF antenna 31 are both included in converter device 20, processing module 34 may control which of RF antennas 30, 31 are connected to RF telemetry module 36, e.g., using a switching circuit within RF telemetry module 36. Accordingly, processing module 34 may control which of RF antennas 30, 31 are transmitting and receiving data. In other words, processing module 34 may be configured to switch between using RF antenna 30 and RF antenna 31 to communicate with medical device 14. When receiving data, processing module 34 may switch between RF antennas 30, 31 based on the signal level acquired by RF antennas 30, 31. For example, processing module 34 may select the antenna that is receiving the strongest signal. In some examples, processing module 34 may switch between RF antennas 30, 31 based on whether errors are detected in data that is received from medical device 14. For example, if errors are detected while receiving data with one of RF antennas 30, 31, then processing module 34 may switch to the other one of RF antennas 30, 31.

As illustrated in FIG. 7, RF antennas 30, 31 may be separated from one another on PCB 54. For example, RF antennas 30, 31 may be separated from one another by a maximum distance on PCB 54. RF antennas 30, 31 that share patterned ground plane 50-4 may be maximally separated from one another by placing RF antennas 30, 31 across from one another with patterned ground plane 50-4 in between, as illustrated in FIG. 7. Although RF antennas 30, 31 are illustrated as maximally separated in FIG. 7, it is contemplated that other arrangements of RF antennas 30, 31 sharing common patterned ground plane 50-4, may be used. The separation between RF antennas 30, 31 may help to realize some spatial diversity regardless of the radiation patterns of each of RF antennas 30, 31. In addition to spatial diversity, pattern diversity can be designed into converter 20 to further improve receive performance. Using separate RF antennas 30, 31 for the same telemetry scheme may provide a higher percentage of coverage. For example, when a null exists in one of RF antennas 30, 31, it may be assumed that the other of RF antennas 30, 31 will have good performance in the area.

Figure 8:
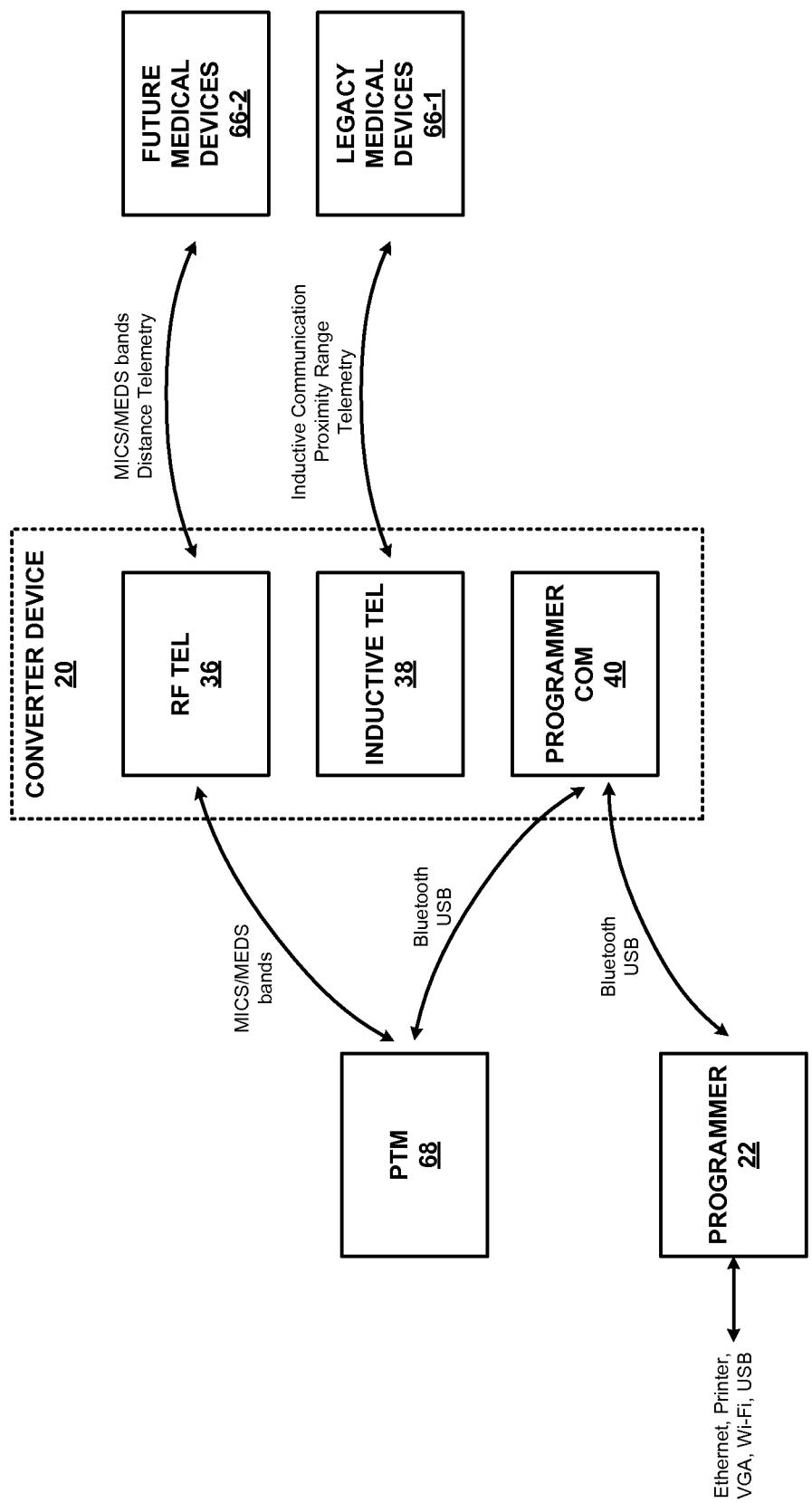
FIG. 8 is a functional block diagram that illustrates the variety of different communication technologies included in an example converter device, and the different devices with which the example converter device may communicate.

FIG. 8 is a functional block diagram that illustrates the variety of different communication technologies that may be included in converter device 20 and the different devices with which converter device 20 may communicate. As illustrated in FIG. 8, converter device 20 may communicate with legacy medical devices 66-1 as well as future medical devices 66-2. Legacy medical devices 66-1 may represent medical devices that use inductive telemetry. Converter device 20 may use inductive telemetry module 38 to communicate with such devices via inductive antenna 32. Converter device 20 may communicate with legacy medical devices 66-1 using inductive communication protocols, for example. Future medical devices 66-2 may represent medical devices that communicate using RF telemetry (e.g., in the MICS/MEDS band). Converter device 20 may use RF telemetry module 36 to communicate with such devices via one of RF antennas 30, 31. Converter device 20 may communicate with future medical devices 66-2 using a MICS/MEDS communication protocol, for example. Converter device 20 may also communicate with programmer 22, as described above, using wired or wireless technologies such as USB or Bluetooth, respectively.

In some examples, converter device 20 may communicate with a patient programmer, such as patient therapy manager 68. Patient therapy manager 68 may represent a device (e.g., a handheld device) that the patient may use to communicate with their medical device in order to retrieve data from their medical device and/or to program data into their medical device. In some examples, patient therapy manager 68 may include RF telemetry functionality for communicating with the patient's medical device. Additionally, patient therapy manager 68 may include a more widely available communication technology such as USB or Bluetooth. Converter device 20 may communicate with patient therapy manager 68 using RF telemetry module 36 and/or programmer communication module 40, depending on which communication technology is included in patient therapy monitor 68.

Figure 9:
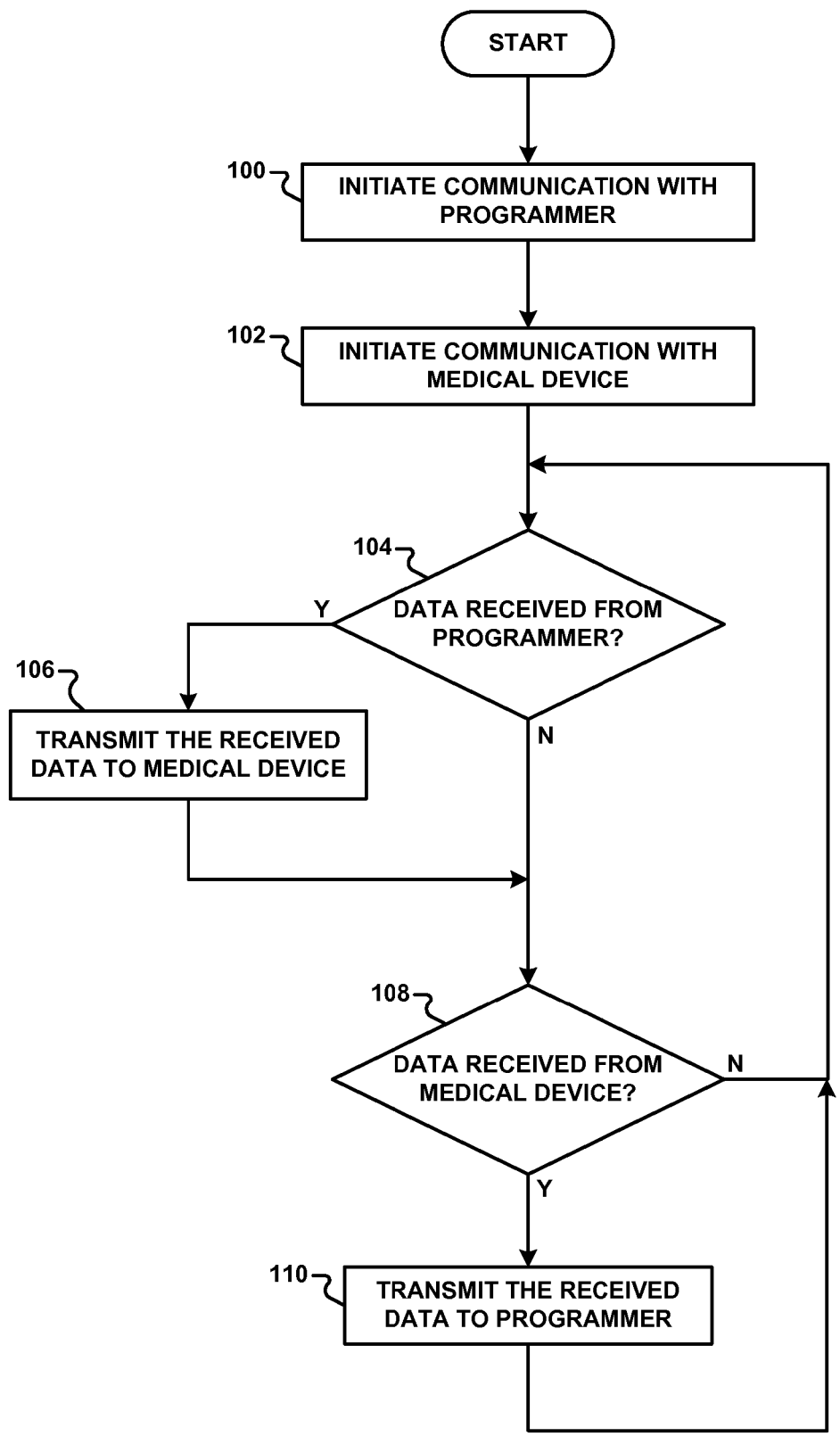
FIG. 9 is a flowchart of a method for providing communication between a programmer and a medical device using a converter device.

FIG. 9 is a flowchart of a method for providing communication between a programmer and a medical device using a converter device. Initially, communication is initiated between programmer 22 and medical device 14 via converter device 20. For example, a user may operate converter device 20 to initiate communication between converter device 20 and programmer 22 (100). Then, the user may operate converter device 20 to initiate communication between converter device 20 and medical device 14 (102). During initiation in blocks (100) and (102), converter device 20 may determine the type of communication technology to use with both medical device 14 and programmer 22. After initiation, programmer 22 may communicate with medical device 14 via converter device 20.

In general, converter device 20 may receive data from programmer 22 and transmit the received data to medical device 14. Additionally, converter device 20 may receive data from medical device 14 and transmit the received data to programmer 22. With respect to block (104), after initiation, converter device 20 may determine whether data is being received from programmer 22 (104). If data is being received from programmer 22 via programmer communication module 40, then converter device 20 may transmit the received data to medical device 14 using at least one of RF telemetry module 36 and inductive telemetry module 38, depending on the type of communication technology included in medical device 14 (106). If data is not being received from programmer 22, then converter device 20 may determine whether data is being received from medical device 14 (108). If data is being received from medical device 14 via at least one of RF telemetry module 36 and inductive telemetry module 38, then converter device 20 may transmit the received data to programmer 22 using programmer communication module 40 (110). If data is not being received from medical device 14, then the method may continue to block (104) to determine whether data is being received from programmer 22.

Although the above description and figures are generally directed to a converter device that serves as an intermediate communication device, the components of the converter device may be integrated into a stand-alone communication device in some examples. For example, the components of the converter device described above may be integrated into a stand-alone programmer that may not act as an intermediate communication device, but, instead, may be used by a clinician to interact directly with a medical device. In other words, the stand-alone programmer may be configured to program medical devices and retrieve data from medical devices without the assistance of other communication devices. The stand-alone programmer may include a PCB having a patterned ground plane, an RF antenna mounted to the PCB, and an inductive antenna mounted to the PCB, as described above. For example, the patterned ground plane of the stand-alone programmer may include open regions over which the inductive antenna is mounted. In some examples, the components of the stand-alone programmer may be enclosed in a housing having a handheld mobile form factor that the clinician may easily manipulate using only a single hand.

Various examples have been described. These and other examples are within the scope of the following claims.

What is claimed is:

1. A device comprising:
   a housing;
   a radio-frequency (RF) antenna associated with the housing;
   a ground plane of the RF antenna within the housing;
   an inductive telemetry antenna within the housing and disposed over a portion of the ground plane; and
   a processing module within the housing and configured to communicate with a medical device using at least one of the RF antenna and the inductive telemetry antenna.

2. The device of claim 1, wherein the ground plane is a continuous conductive layer.

3. The device of claim 2, wherein the ground plane defines one or more openings in the portion that is located under the inductive telemetry antenna.

4. The device of claim 3, wherein the ground plane defines a plurality of protrusions, and wherein the one or more openings are defined by the protrusions.

5. The device of claim 3, wherein the inductive telemetry antenna comprises a wire that is wound to define a core region of the inductive telemetry antenna, and wherein the core region of the inductive telemetry antenna is located over the one or more openings.

6. The device of claim 5, wherein the one or more openings under the core region of the inductive telemetry antenna comprise approximately half of the area under the core region, and wherein the ground plane comprises the remaining area under the core region.

7. The device of claim 5, wherein the one or more openings under the core region of the inductive telemetry antenna comprise approximately thirty percent of the area under the core region, and wherein the ground plane comprises the remaining area under the core region.

8. The device of claim 1, further comprising a printed circuit board (PCB) including the ground plane of the RF antenna, wherein the RF antenna is mounted on the PCB, wherein the processing module is mounted on the PCB, and wherein the inductive telemetry antenna is mounted on the PCB over the portion of the ground plane.

9. The device of claim 1, wherein the housing encloses the RF antenna, the ground plane, the inductive telemetry antenna, and the processing module, and wherein the housing has a handheld form factor that is configured to be held in a single hand.

10. The device of claim 1, wherein the RF antenna is a first RF antenna, wherein the device further comprises a second RF antenna, and wherein the processing module is configured to:
   receive first data from a computing device using the second RF antenna; and
   transmit the first data to the medical device using at least one of the first RF antenna and the inductive telemetry antenna.

11. The device of claim 1, wherein the RF antenna is a first RF antenna, wherein the device further comprises a second RF antenna, wherein the processing module is configured to communicate with the medical device using the second RF antenna, and wherein the ground plane of the first RF antenna is also a ground plane of the second RF antenna.

12. The device of claim 1, wherein the RF antenna is configured to transmit and receive signals in a frequency band from approximately 401 MHz to 406 MHz.

13. The device of claim 1, wherein the inductive telemetry antenna is configured to transmit and receive signals from approximately 100 KHz to approximately 15 MHz.

14. The device of claim 1, wherein the medical device is configured for implantation in a patient.

15. The device of claim 1, further comprising a programmer communication module that is configured to communicate with a programmer of the medical device using wired communication.

16. The device of claim 1, wherein:
   the RF antenna is configured to transmit and receive signals in a first frequency band;
   the inductive telemetry antenna is configured to transmit and receive signals in a second frequency band; and
   frequencies of the first frequency band are different than frequencies of the second frequency band.

17. A device comprising:
   a radio-frequency (RF) antenna;
   a ground plane of the RF antenna;
   a printed circuit board (PCB) including the ground plane of the RF antenna, wherein the RF antenna is mounted on the PCB, wherein the ground plane is a continuous conductive layer that defines a plurality of protrusions, and wherein the plurality of protrusions define one or more openings;
   an inductive telemetry antenna mounted on the PCB over the ground plane, wherein the inductive telemetry antenna comprises a wire that is wound to define a core region of the inductive telemetry antenna, and wherein the core region of the inductive telemetry antenna is located over the one or more openings; and
   a processing module mounted on the PCB that is configured to communicate with a medical device using at least one of the RF antenna and the inductive telemetry antenna.

18. The device of claim 17, further comprising a housing that encloses the PCB, the RF antenna, the ground plane, the inductive telemetry antenna, and the processing module, and wherein the housing has a handheld form factor that is configured to be held in a single hand.

19. The device of claim 17, wherein the one or more openings under the core region of the inductive telemetry antenna comprise approximately half of the area under the core region, and wherein the ground plane comprises the remaining area under the core region.

20. The device of claim 17, wherein the one or more openings under the core region of the inductive telemetry antenna comprise approximately thirty percent of the area under the core region, and wherein the ground plane comprises the remaining area under the core region.

21. The device of claim 17, wherein the RF antenna is a first RF antenna, wherein the device further comprises a second RF antenna, and wherein the processing module is configured to:
   receive first data from a computing device using the second RF antenna; and
   transmit the first data to the medical device using at least one of the first RF antenna and the inductive telemetry antenna.

22. A device comprising:
   a first radio-frequency (RF) antenna;
   an inductive telemetry antenna;
   a second RF antenna;
   a processing module configured to:
      communicate with a medical device using the first RF antenna;
      communicate with the medical device using the inductive telemetry antenna;
      receive first data from a computing device using the second RF antenna; and
      transmit the first data to the medical device; and
   a housing that encloses the processing module, the inductive telemetry antenna, and the first and second RF antennas, and wherein the housing has a handheld form factor that is configured to be held in a single hand.

23. The device of claim 22, wherein the processing module is configured to:
   receive second data from the medical device; and
   transmit the second data to the computing device using the second RF antenna.

24. The device of claim 22, further comprising a third RF antenna, wherein the processing module is configured to communicate with the medical device using the third RF antenna.

* * * * *